United States Patent [19]
Anderson

[11] Patent Number: 6,099,799
[45] Date of Patent: Aug. 8, 2000

[54] APPARATUS FOR ULTRAVIOLET DISINFECTION OF WATER

[75] Inventor: Ellis D. Anderson, Saugus, Calif.

[73] Assignee: Pura, Inc., Valencia, Calif.

[21] Appl. No.: 09/042,140

[22] Filed: Mar. 13, 1998

Related U.S. Application Data

[60] Provisional application No. 60/039,085, Mar. 14, 1997.

[51] Int. Cl.$^7$ ....................................................... A61L 2/00
[52] U.S. Cl. ........................... 422/24; 210/256; 210/748; 250/455.11; 422/186.3
[58] Field of Search .............................. 422/24, 1, 186.3; 250/455.11; 210/748, 256

[56] References Cited

U.S. PATENT DOCUMENTS

| | | |
|---|---|---|
| 3,836,781 | 9/1974 | Ellison . |
| 3,894,236 | 7/1975 | Hazelrigg . |
| 3,926,556 | 12/1975 | Boucher ................................. 422/21 |
| 4,069,153 | 1/1978 | Gunther ................................. 422/24 |
| 4,141,830 | 2/1979 | Last ........................................ 422/24 |
| 4,273,660 | 6/1981 | Beitzel ................................... 422/24 |
| 4,528,093 | 7/1985 | Winer . |
| 4,769,131 | 9/1988 | Noll et al. . |
| 4,968,437 | 11/1990 | Noll et al. . |
| 4,971,687 | 11/1990 | Anderson . |
| 5,004,541 | 4/1991 | Noll et al. . |
| 5,069,782 | 12/1991 | Moyher, Jr. et al. . |
| 5,230,792 | 7/1993 | Sauska et al. . |
| 5,445,729 | 8/1995 | Monroe et al. . |
| 5,653,877 | 8/1997 | Mark . |

*Primary Examiner*—Krisanne Thornton
*Attorney, Agent, or Firm*—Kelly Bauersfeld Lowry & Kelley, LLP.

[57] ABSTRACT

A water treatment and disinfection apparatus is provided, which has separate flow channels to allow entry and exit of separate streams of water through the apparatus, with an ultraviolet light source emitting rays through first and second ultraviolet transparent sleeves having an annular space therebetween to form an inner flow channel and an annular space between the second sleeve and an ultraviolet resistant pressure vessel. The apparatus of the invention is specially suited for disinfection of water in reverse osmosis water purification systems, whereby pre-reverse osmosis (untreated) water and post-reverse osmosis (treated) water are directed inside the apparatus of the invention to be separately and simultaneously disinfected by ultraviolet rays and again separately exit the apparatus.

10 Claims, 3 Drawing Sheets

APPARATUS FOR ULTRAVIOLET DISINFECTION OF WATER

This application claims benefit of provisional application No. 60/039,085 filed Mar. 14, 1997.

BACKGROUND OF THE INVENTION

This invention generally relates to water treatment and disinfection, and particularly to a device that utilizes ultraviolet ("UV") rays to disinfect water. More specifically, the device of this invention addresses the need for UV disinfection related to water treatment processes such as those that use reverse osmosis or filtration, where it is important to disinfect the water both before and after the water treatment process.

Water purification and disinfection units are well known in the art. Some use mechanical filtration to remove impurities suspended as particles in the water, while others use a combination system, such as mechanical filtration and ultraviolet rays to purify, sterilize and disinfect the water. Other water treatment systems exist, which use well known reverse osmosis technology to purify the water. In various water treatment processes, such as those using reverse osmosis or other filtration systems, it would be desirable and important to disinfect the water both before and after the water treatment process. As an example, disinfection of the pre-reverse osmosis (untreated) water is important because bacteria present in the water can cause biofouling of the reverse osmosis membrane, and disinfection of the post-reverse osmosis (treated) water is important because of the possibility that bacterial contamination has been introduced during the reverse osmosis process or during the storage of the treated water. In disinfecting the untreated and treated water, it would also be desirable to be able to maintain those bodies of water separate and apart from each other during the disinfection process.

The present invention satisfies these needs by providing a water treatment apparatus and process which utilizes separate chambers for flow of untreated and treated water which are disinfected by ultraviolet rays that can pass through one chamber to the other. The flow capacity of the device of the invention is not limited, and can be adapted for manufacture in various sizes to meet the particular flow rate needs of the desired water treatment process. The size of the device of the invention can be varied according to the available technology for producing the desired UV light intensity.

SUMMARY OF THE INVENTION

In accordance with the invention, a water treatment apparatus is provided, wherein an ultraviolet (UV) light source is surrounded by independent and separate chambers for flow of separate streams of water, with the UV light reaching and disinfecting the water in those chambers.

In the preferred form, a UV light source is housed inside a first UV transparent tube or sleeve, which is in turn housed inside a second UV transparent tube or sleeve, with an annular space between the first and second sleeves. The first sleeve is closed at one end and sealed at the other so as to prevent water or other liquid from coming into direct contact with the UV light source which is connected to a power source. The second UV transparent sleeve is further housed within a pressure vessel or container that is resistant to UV light, with an annular space between the second sleeve and the pressure vessel. In this manner, an inner flow channel is formed between the first and second UV transparent sleeves, and an outer flow channel is formed between the second sleeve and the pressure vessel. The upper and lower portions of the two flow channels are sealed with each channel having an inlet port and an exit port to allow separate streams of water to enter the channels, be treated with UV rays, and then exit the channels.

With this construction, treated water can enter the inner flow channel through its inlet port, and untreated water can enter the outer channel through its inlet port. After being disinfected by the UV rays passing through the bodies of water in the separate channels, the UV treated streams of water exit through the exit ports. The flow pattern whereby the treated water flows through the inner channel and the untreated water flows through the outer channel is preferred, because by having the UV rays first pass through the treated/cleaner water in the inner channel, UV transmission will not be inhibited by the impurities in the untreated water in the outer channel. According to alternative embodiments of the invention, other flow patterns with various flow channel configurations can also be utilized.

Other features and advantages of the present invention will become more apparent from the following detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF ALTERNATIVE EMBODIMENTS

Figure 1:
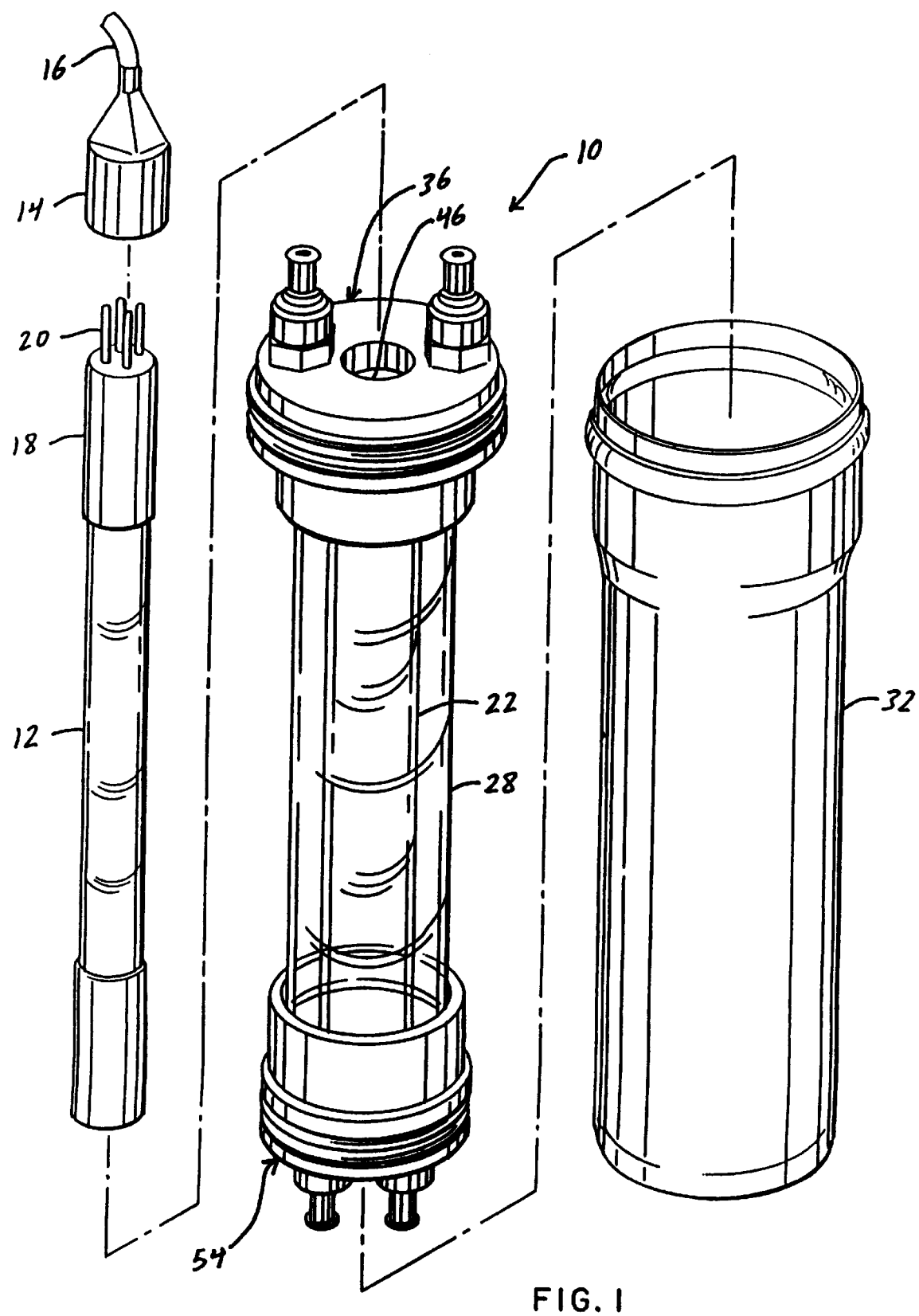
FIG. 1 is an exploded perspective view illustrating a water treatment apparatus embodying the novel features of the invention, including a UV light source, spaced apart ultraviolet transparent sleeves with top and bottom end plug units, and a pressure vessel, shown in a partially unassembled condition.

As shown in exemplary drawings, a water treatment apparatus referred to generally by the reference numeral 10 is provided with an ultraviolet (UV) lamp 12, e.g., an ozone or non-ozone lamp, that connects to a power source (not shown) via a connecting plug 14 and wire 16. A terminal 18 is provided with the customary power prongs 18 which go into electrical contacts in plug 14.

The UV lamp 12 is housed inside a first UV transparent cylinder or sleeve 22, which is sized slightly larger in diameter than the outside diameter of the UV lamp 12 and has a closed lower end 24 and an open upper end 26. The first UV transparent sleeve 22 is housed within a second UV transparent cylinder or sleeve 28, with an annular space therebetween so as to create an inner flow channel 30. The first sleeve 22 and the second sleeve 28 are preferably made of quartz, but can also be made of other UV transparent materials. A pressure vessel 32, preferably made of stainless steel, or alternatively of any other UV resistant material suitable to withstand pressure, is provided to house and contain the entire assembly of the first sleeve 22 and the second sleeve 28, such that there is an annular space between the second UV transparent sleeve 28 and the pressure vessel 32, which forms a outer flow channel 34. Accordingly, in this manner, two independent channels for passage of water are created: an outer channel 34, defined by the space between the inside wall of the pressure vessel 32 and the outside wall of the second UV transparent sleeve 28; and an inner channel 30, defined by the space between the inside wall of the second UV transparent sleeve 28 and the outside wall of the first UV transparent sleeve 22.

Figure 2:
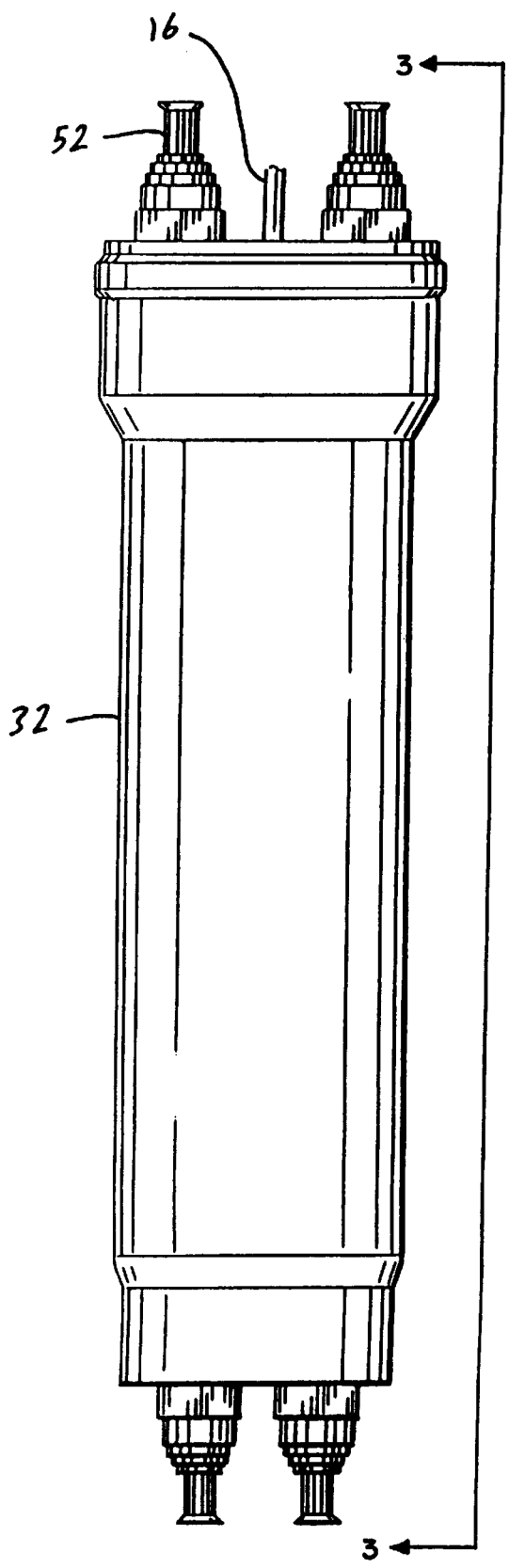
FIG. 2 is perspective view of the water treatment apparatus of FIG. 1, but illustrating the apparatus in an assembled condition.
Figure 3:
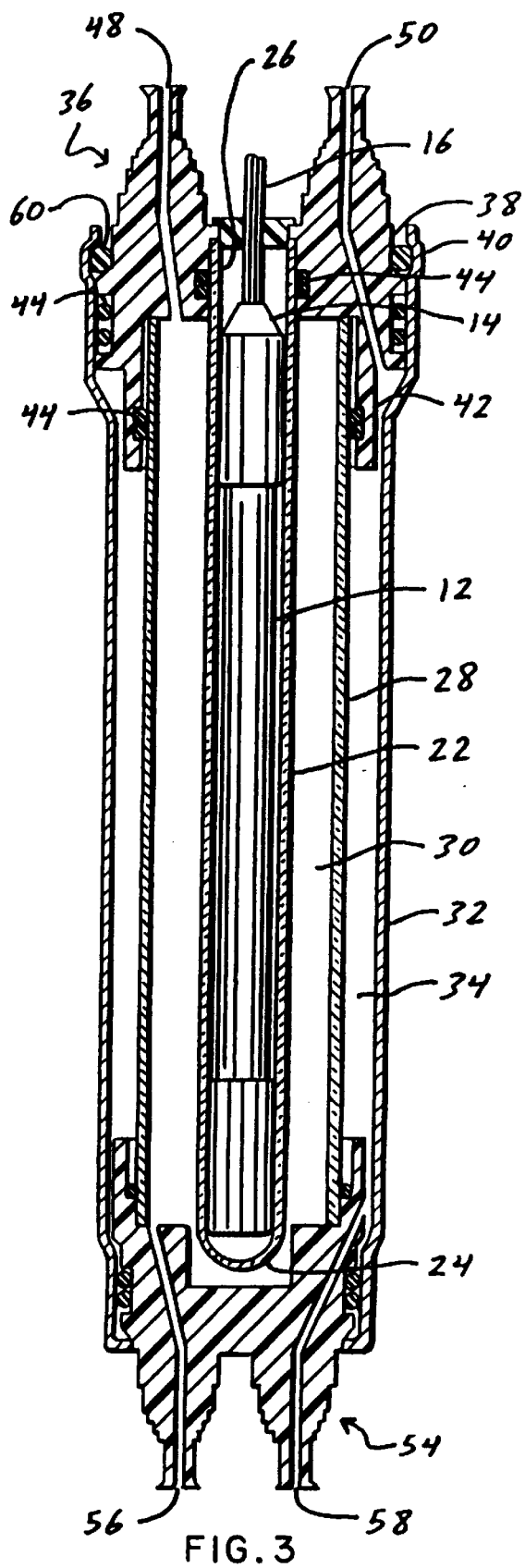
FIG. 3 is a cross-sectional view of the water treatment apparatus taken along line 3—3 of FIG. 2.

The upper end of the apparatus is provided with a top plug unit 36 to close off the top openings in the outer channel 34, the inner channel 30, and the first UV transparent sleeve 22. As shown in FIGS. 1, 2 and 3, the top plug unit 36 has a generally cylindrical shape with a larger diameter at its upper end 38 to frictionally fit inside the upper end 40 of the pressure vessel 32, and a smaller diameter at its lower end 42 which extends over the second UV transparent sleeve 28. A pair of O-rings 44 are located in a recess over the upper end 38 of the top plug unit 36 to seal against the pressure vessel 32, a pair of O-rings 44 are located between the lower end 42 of the top plug unit 36 to seal against the exterior of the second UV transparent sleeve 28, and a pair of O-rings 44 are also located between an interior portion of the top plug unit and the exterior of the first UV transparent sleeve 22. In this manner, the upper portions of the inner flow channel 30 and the outer flow channel 34 are sealed against the top plug unit. In addition, a centrally located hole or recess 46 in the top plug unit 36 is sized slightly larger in diameter than the outside diameter of the first sleeve to allow the first sleeve 22 to extend inside the recess 46, as well as to allow the plug 14 to frictionally fit inside the top plug unit and connect to the power prongs 20 of the UV lamp 12 and support the UV lamp 12 inside the first UV transparent sleeve 22. In this manner, the UV lamp 12 does not come into direct contact with any water entering the unit. Additionally, a top inner port 48 is provided in the top plug unit 36 to allow fluid communication between the outside of the apparatus and the inner flow channel 30, and a top outer port 50 in the top plug unit 36 allows fluid communication between the outside and the outer flow channel. Each of these two ports, 48 and 50, is provided with a connection plug 52 which can be attached to a tube (not shown) directing water (or other fluid) supply lines to the apparatus of the invention.

A similar bottom plug unit 54 is provided at the opposite end of the apparatus to close and seal the lower ends of the inner flow channel 30 and the outer flow channel 34. As shown in FIG.3, the bottom plug unit 54 also utilizes O-rings 44 to seal the plug unit against the interior of the pressure vessel 32 and against the exterior of the second UV transparent sleeve 28. Similarly, the bottom plug unit 54 is provided with a bottom inner port 56 to allow fluid communication between the outside of the apparatus and the inner flow channel 30, as well as a bottom outer port 58 to allow fluid communication between the outside and the outer flow channel 34. In this manner, water or other fluid that is to be disinfected can be directed to enter the inner flow channel 30 and outer flow channel 34 independently and separately, undergo UV disinfection, and exit the channels separately. The top and bottom plug units, 36 and 54, are preferably made of a moldable and machinable plastic, such as high density polypropylene, which is rust and corrosion resistant. Stainless steel may also be used, but is not as readily workable as plastic to machine the recess 46 for the first sleeve.

Once the assembly of the first and second UV transparent sleeves and the top and bottom plug units is completed, the assembly is positioned inside the pressure vessel 32. The lower end of the pressure vessel 32 is slightly curved inward so as to prevent the assembly from sliding out of the pressure vessel. A retaining ring 60 is also provided between the top plug unit 36 and the interior of the pressure vessel to secure the assembly inside the pressure vessel so that it cannot become dislodged under water pressure.

In the preferred embodiment of the invention, for example, in conjunction with a reverse osmosis water treatment system, where it is important and desirable to disinfect the water both before and after the water treatment process, the pre-reverse osmosis (untreated) water is directed through the top outer port 50 to enter the outer flow channel 34, and the post-reverse osmosis (treated) water can be directed through the top inner port 48 to enter the inner flow channel 30. Inside the separate water chambers, the pre-reverse osmosis and the post-reverse osmosis bodies of water remain separate, and are treated through exposure to the UV rays of the UV lamp 12 which travel through the transparent first and second sleeves, 22 and 28. After exposure to the UV rays and the resulting disinfection, the stream of water flowing through the outer channel 34 exits through the bottom outer port 58, and the stream of water flowing through the inner channel 30 exits through the bottom inner port 56. (It should be noted that, the flow direction through each of the inner and outer channels is reversible). This flow pattern is recommended because if the untreated water were to pass through the inner channel 30, it would inhibit the transmission of UV light into the outer channel 34 due to impurities in the untreated water.

Figure 4:
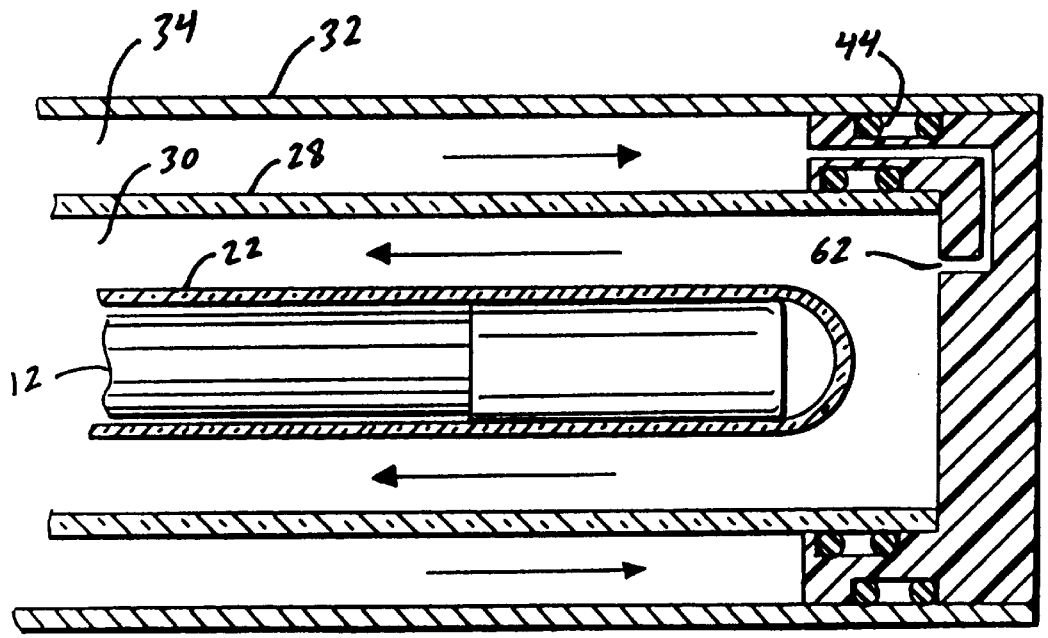
FIG. 4 is a partial cross-sectional view of an alternative embodiment of the water treatment apparatus of the invention illustrated in FIG. 1.
Figure 5:
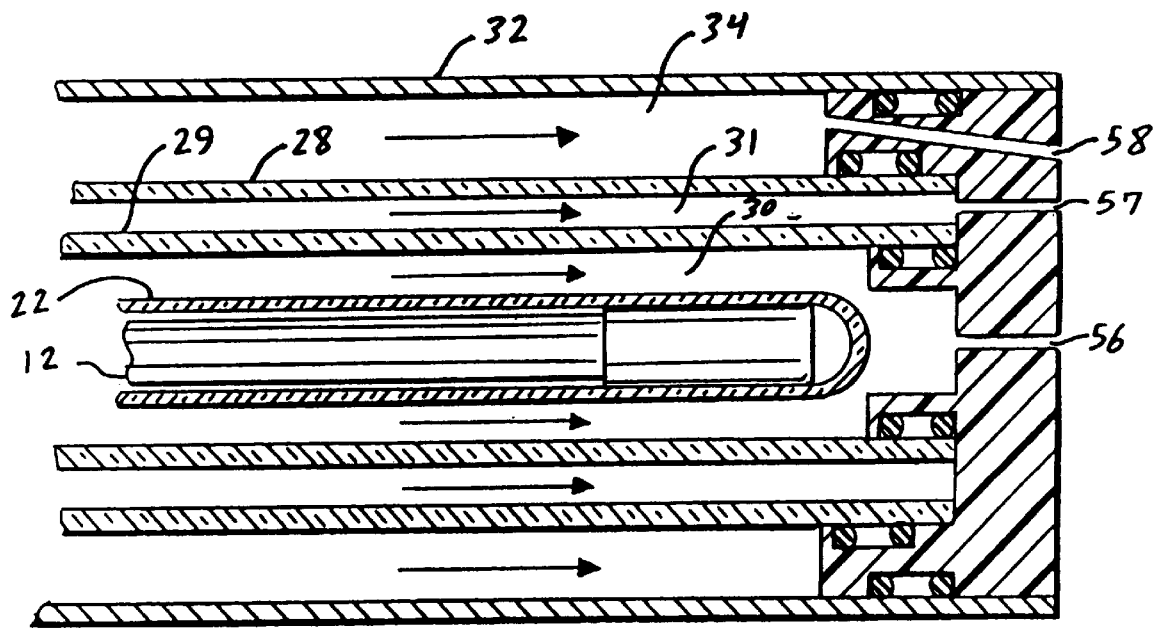
FIG. 5 is a partial cross-sectional view of another alternative embodiment of the water treatment apparatus of the invention illustrated in FIG.

According to alternative embodiments of the invention, shown be way of example, in FIGS. 4 and 5, various water flow patterns may be utilized. For example, as opposed to two independent flows shown and discussed above, as shown in FIG. 4 (which only shows a schematic of the bottom end of the apparatus of the invention), the apparatus can be modified to achieve a single flow of water that passes by the UV light source two times, once inside the outer channel 34 and another time inside the inner channel 30. In this alternative embodiment, the two connection plugs 52 in the bottom plug unit 54 are eliminated, and the water the water is directed from the outer channel into the inner channel through a port 62 located in the bottom plug unit 54.

According to another alternative embodiment, shown by way of example in FIG. 5, a triple pass system can be used, whereby an additional flow channel can be added. This would require modification of the top plug unit 36 and the bottom plug unit 54 so as to have three connection plugs on each of the top and bottom plug units; e.g., resulting in bottom inner port 56, bottom intermediate port 57 and bottom outer port 58, with a similar arrangement for the three top ports. This embodiment would also require the addition of a third UV transparent cylinder or sleeve 29 positioned and spaced between the first sleeve 22 and the second sleeve 28 so as to result in three flow channels; i.e., the inner flow channel 30, an intermediate flow channel 31, and the outer flow channel 34, each with independent water flows. A variation of this alternative embodiment (not shown) can also be used so that two of the flow channels are inter-connected to create two independent flows, one with a single pass and one with a double pass. Yet another variation of this alternative (not shown) can be used to accomplish a triple pass of a single flow of water. This variation would require connecting ports in the bottom plug unit 54 similar to that shown in FIG. 4. The concept of various flow patterns with various number of passes by the UV lamp can be expanded as necessary to as many flow channels and passes as needed.

The water treatment apparatus of the invention thus provides a versatile yet relatively simple device and process for simultaneous disinfection of separate streams of water or other fluid by ultraviolet rays.

A variety of further modifications and improvements in and to the water treatment apparatus of the invention will be apparent to persons skilled in the art. Accordingly, no limitation on the invention is intended by way of the foregoing description and accompanying drawings, except as set forth in the appended claims.

What is claimed is:

1. An apparatus for liquid disinfection, comprising:
   a hollow elongate vessel;
   an outer hollow elongate sleeve, capable of passing disinfecting radiation therethrough, located within said hollow vessel and cooperating therewith to define an annular shaped fluid tight outer flow channel between itself and said hollow vessel;
   an inner hollow elongate sleeve, capable of passing disinfecting radiation therethrough, located within said outer hollow elongate sleeve and cooperating therewith to define an annular shaped fluid tight inner flow channel between itself and said outer hollow elongate sleeve, wherein said inner flow channel is out of fluid communication relative to said outer flow channel, said inner hollow elongate sleeve forming an interior space;
   a disinfecting radiation source positioned in the interior space of said inner hollow elongate sleeve to irradiate liquid in said inner flow channel and said outer flow channel;
   means for circulating a liquid through said inner flow channel; and
   means for circulating a liquid through said outer flow channel.

2. The liquid disinfection apparatus of claim 1 wherein said inner hollow elongate sleeve and said outer hollow elongate sleeve are formed of quartz material which is transparent to said irradiation.

3. The liquid disinfection apparatus of claim 1 wherein said disinfecting radiation is in the form of ultraviolet rays.

4. The liquid disinfection apparatus of claim 1 wherein said hollow elongate vessel is formed of an irradiation resistant material.

5. The liquid disinfection apparatus of claim 1 wherein said inner hollow elongate sleeve is closed at a first end.

6. The liquid disinfection apparatus of claim 1 further including means for sealing said radiation source within said interior space of said inner hollow elongate sleeve from said inner and outer flow channels.

7. The liquid disinfection apparatus of claim 1 wherein said means for circulating liquid through said inner flow channel and said outer flow channel comprises an inlet port and an outlet port.

8. The liquid disinfection apparatus of claim 1 wherein said means for circulating liquid through said inner flow channel comprises an inlet port and an outlet port, both said ports in fluid communication with said inner flow channel.

9. The liquid disinfection apparatus of claim 1 wherein said means for circulating liquid through said outer flow channel comprises an inlet port and an outlet port, both said ports in fluid communication with said outer flow channel.

10. A method for disinfection of liquid comprising the steps of:
    forming at least two concentric liquid flow channels about a disinfecting radiation source, said at least two concentric flow channels that are out of fluid communication relative to one another and separated by at least one sleeve capable of passing disinfecting radiation therethrough, and said radiation source being sealed from said liquid flow; and
    passing the liquid through said at least two concentric flow channels for irradiation and disinfection.

* * * * *